(12) United States Patent
Burkholz

(10) Patent No.: US 10,842,985 B2
(45) Date of Patent: Nov. 24, 2020

(54) NEEDLELESS CONNECTOR AND ACCESS PORT DISINFECTION CLEANER AND ANTIMICROBIAL PROTECTION CAP

(71) Applicant: Becton, Dickinson and Company, Franklin Lakes, NJ (US)

(72) Inventor: Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 159 days.

(21) Appl. No.: 15/216,307

(22) Filed: Jul. 21, 2016

(65) Prior Publication Data

US 2016/0325089 A1    Nov. 10, 2016

Related U.S. Application Data

(63) Continuation of application No. 13/766,540, filed on Feb. 13, 2013, now Pat. No. 9,399,125.

(51) Int. Cl.
*A61M 39/16* (2006.01)
*A61M 5/00* (2006.01)
(Continued)

(52) U.S. Cl.
CPC .......... *A61M 39/162* (2013.01); *A61M 5/001* (2013.01); *A61M 39/16* (2013.01); *A61M 39/20* (2013.01); *A61M 5/31* (2013.01)

(58) Field of Classification Search
CPC .......... A61M 39/20; A61M 2005/3104; A61M 2039/1072; A61M 5/002;
(Continued)

(56) References Cited

U.S. PATENT DOCUMENTS

| 2,961,682 | A |   | 11/1960 | Wurmbock et al. |
| 3,987,930 | A | * | 10/1976 | Fuson .................. A61M 39/20 |
|           |   |   |         |                               220/287 |

(Continued)

FOREIGN PATENT DOCUMENTS

| EP | 1 649 890 A1 | 4/2006 |
| EP | 2 606 930 A1 | 6/2013 |

(Continued)

OTHER PUBLICATIONS

"Corrected Petition for Inter Partes Review Under 35 U.S.C. .sctn. 311-319 and 37 C.F.R. .sctn. 42,100 et seq.," USPTO, Patent Trial and Appeal Board, *Excelsior Medical Corporation v. Becton, Dickinson and Company*, Case IPR2014-00880, U.S. Pat. No. 8,740,864, pp. 1-48, Jun. 23, 2014.

(Continued)

*Primary Examiner* — Scott J Medway
(74) *Attorney, Agent, or Firm* — Kirton McConkie; Craig Metcalf; Kevin Stinger

(57) ABSTRACT

A protective cap having a first cap and a second cap that are removably coupled together for use in short-term and long-term antimicrobial treatment of needleless connectors and access ports of an infusion system. The instant invention further provides a protective cap having a first cap and a second cap that each coupled to a different surface of a component of an infusion system, such as a syringe. The instant invention further provides a strip containing a plurality of disposable protective caps.

12 Claims, 8 Drawing Sheets

(51) Int. Cl.
*A61M 39/20* (2006.01)
*A61M 5/31* (2006.01)

(58) Field of Classification Search
CPC ........ A61M 2005/312; A61M 2209/06; A61M 5/3202; A61M 5/5086; A61M 25/00; A61M 25/16; A61M 25/18; A61M 39/00; A61M 39/10
See application file for complete search history.

(56) References Cited

U.S. PATENT DOCUMENTS

| | | | |
|---|---|---|---|
| 4,280,632 A | 7/1981 | Yuhara | |
| 4,282,891 A | 8/1981 | Duceppe | |
| 4,354,490 A | 10/1982 | Rogers | |
| 4,417,890 A | 11/1983 | Dennehey et al. | |
| 4,432,764 A | 2/1984 | Lopez | |
| 4,440,207 A | 4/1984 | Genatempo et al. | |
| 4,444,310 A | 4/1984 | Odell | |
| 4,584,192 A | 4/1986 | Dell et al. | |
| 4,624,664 A * | 11/1986 | Peluso | A61M 39/165 |
| | | | 604/256 |
| 4,626,664 A | 12/1986 | Grise | |
| 4,655,762 A | 4/1987 | Rogers | |
| 4,671,306 A | 6/1987 | Spector | |
| 4,716,032 A | 12/1987 | Westfall et al. | |
| 4,753,358 A | 6/1988 | Virca et al. | |
| 4,778,447 A | 10/1988 | Velde et al. | |
| 4,838,875 A * | 6/1989 | Somor | A61J 1/10 |
| | | | 604/247 |
| 4,915,934 A | 4/1990 | Tomlinson | |
| 4,925,668 A | 5/1990 | Khan et al. | |
| 4,989,733 A | 2/1991 | Patry | |
| 4,991,629 A | 2/1991 | Ernesto et al. | |
| 5,023,082 A | 6/1991 | Friedman et al. | |
| 5,195,957 A | 3/1993 | Tollini | |
| 5,242,425 A | 9/1993 | White et al. | |
| 5,334,388 A | 8/1994 | Hoang et al. | |
| 5,335,373 A | 8/1994 | Dresdner, Jr. et al. | |
| 5,512,199 A | 4/1996 | Khan et al. | |
| 5,547,662 A | 8/1996 | Khan et al. | |
| 5,554,106 A | 9/1996 | Layman-Spillar et al. | |
| 5,554,135 A | 9/1996 | Menyhay | |
| 5,569,207 A | 10/1996 | Gisselberg et al. | |
| 5,616,338 A | 4/1997 | Fox, Jr. et al. | |
| 5,620,424 A | 4/1997 | Abramson | |
| 5,639,310 A | 6/1997 | Giampaolo, Jr. | |
| 5,641,464 A | 6/1997 | Briggs, III et al. | |
| 5,686,096 A | 11/1997 | Khan et al. | |
| 5,694,978 A | 12/1997 | Heilmann et al. | |
| 5,702,017 A | 12/1997 | Goncalves | |
| 5,706,944 A | 1/1998 | Hoang et al. | |
| 5,722,537 A | 3/1998 | Sigler | |
| 5,743,884 A | 4/1998 | Hasson et al. | |
| 5,792,120 A | 8/1998 | Menyhay | |
| 5,817,344 A | 10/1998 | Hoang et al. | |
| 5,861,440 A | 1/1999 | Gohla et al. | |
| 5,954,957 A | 9/1999 | Chin-Loy et al. | |
| 5,989,229 A | 11/1999 | Chiappetta | |
| 6,045,539 A | 4/2000 | Menyhay | |
| 6,051,609 A | 4/2000 | Yu et al. | |
| 6,116,468 A | 9/2000 | Nilson | |
| 6,117,114 A | 9/2000 | Paradis | |
| 6,196,998 B1 | 3/2001 | Jansen et al. | |
| 6,227,391 B1 | 5/2001 | King | |
| 6,337,357 B1 | 1/2002 | Fukunishi et al. | |
| 6,413,539 B1 | 7/2002 | Shalaby | |
| 6,488,942 B1 | 12/2002 | Ingemann | |
| 6,523,686 B1 | 2/2003 | Bae | |
| RE38,145 E | 6/2003 | Lynn | |
| 6,708,363 B2 | 3/2004 | Larsen | |
| 6,846,846 B2 | 1/2005 | Modak et al. | |
| 6,861,060 B1 | 3/2005 | Luriya et al. | |
| 6,911,025 B2 | 6/2005 | Miyahara | |
| 6,994,315 B2 | 2/2006 | Ryan et al. | |
| 7,083,605 B2 | 8/2006 | Miyahara | |
| 7,198,611 B2 | 4/2007 | Connell et al. | |
| 7,198,800 B1 | 4/2007 | Ko | |
| 7,268,165 B2 | 9/2007 | Greten et al. | |
| 7,282,186 B2 | 10/2007 | Lake, Jr. et al. | |
| 7,452,349 B2 | 11/2008 | Miyahara | |
| 7,682,561 B2 | 3/2010 | Davis et al. | |
| 7,704,935 B1 | 4/2010 | Davis et al. | |
| 7,762,524 B2 * | 7/2010 | Cawthon | A61M 39/165 |
| | | | 251/149.6 |
| 7,763,006 B2 | 7/2010 | Tennican | |
| 7,780,794 B2 * | 8/2010 | Rogers | A61L 2/18 |
| | | | 134/6 |
| 7,828,186 B2 | 11/2010 | Wales | |
| 7,922,701 B2 | 4/2011 | Buchman | |
| 8,065,773 B2 | 11/2011 | Vaillancourt et al. | |
| 8,113,731 B2 | 2/2012 | Cable, Jr. et al. | |
| 8,162,899 B2 | 4/2012 | Tennican | |
| 8,167,847 B2 | 5/2012 | Anderson et al. | |
| 8,172,825 B2 * | 5/2012 | Solomon | A61M 39/162 |
| | | | 604/256 |
| 8,491,546 B2 | 7/2013 | Hoang et al. | |
| 8,740,864 B2 | 6/2014 | Hoang et al. | |
| 8,784,388 B2 * | 7/2014 | Charles | A61M 39/14 |
| | | | 604/199 |
| 9,192,449 B2 * | 11/2015 | Kerr | A61M 39/20 |
| 9,283,367 B2 * | 3/2016 | Hoang | A61M 39/02 |
| 9,283,369 B2 | 3/2016 | Ma et al. | |
| 9,700,710 B2 * | 7/2017 | Anderson | A61M 5/31511 |
| 9,707,350 B2 * | 7/2017 | Anderson | A61M 5/31 |
| 10,166,339 B2 * | 1/2019 | Solomon | A61M 39/162 |
| 2001/0016589 A1 | 8/2001 | Modak et al. | |
| 2002/0144705 A1 | 10/2002 | Brattesani et al. | |
| 2003/0072781 A1 | 4/2003 | Pelerin | |
| 2003/0109853 A1 | 6/2003 | Harding et al. | |
| 2003/0153865 A1 | 8/2003 | Connell et al. | |
| 2003/0162839 A1 | 8/2003 | Symington et al. | |
| 2004/0004019 A1 | 1/2004 | Busch | |
| 2004/0039349 A1 | 2/2004 | Modak et al. | |
| 2004/0258560 A1 | 12/2004 | Lake, Jr. et al. | |
| 2005/0124970 A1 | 6/2005 | Kunin et al. | |
| 2005/0147524 A1 | 7/2005 | Bousquet | |
| 2005/0147525 A1 | 7/2005 | Bousquet | |
| 2005/0222542 A1 | 10/2005 | Burkholz et al. | |
| 2006/0030827 A1 | 2/2006 | Raulerson et al. | |
| 2006/0165751 A1 | 7/2006 | Chudzik et al. | |
| 2006/0239954 A1 | 10/2006 | Sancho | |
| 2007/0112333 A1 | 5/2007 | Hoang et al. | |
| 2007/0202177 A1 | 8/2007 | Hoang | |
| 2007/0225660 A1 | 9/2007 | Lynn | |
| 2007/0282280 A1 | 12/2007 | Tennican | |
| 2008/0019889 A1 | 1/2008 | Rogers et al. | |
| 2008/0027399 A1 | 1/2008 | Harding et al. | |
| 2008/0033371 A1 | 2/2008 | Updegraff et al. | |
| 2008/0075761 A1 | 3/2008 | Modak et al. | |
| 2008/0086091 A1 | 4/2008 | Anderson et al. | |
| 2008/0095680 A1 | 4/2008 | Steffens et al. | |
| 2008/0147047 A1 | 6/2008 | Davis et al. | |
| 2008/0177250 A1 | 7/2008 | Howlett et al. | |
| 2008/0182921 A1 | 7/2008 | Suh et al. | |
| 2009/0008393 A1 | 1/2009 | Howlett et al. | |
| 2009/0028750 A1 | 1/2009 | Ryan | |
| 2009/0028756 A1 | 1/2009 | Shahriari | |
| 2009/0062766 A1 | 3/2009 | Howlett et al. | |
| 2009/0149818 A1 | 6/2009 | Timm | |
| 2009/0149819 A1 | 6/2009 | Chelak | |
| 2009/0175759 A1 | 7/2009 | Davis et al. | |
| 2010/0000040 A1 | 1/2010 | Shaw et al. | |
| 2010/0047123 A1 | 2/2010 | Solomon et al. | |
| 2010/0049170 A1 | 2/2010 | Solomon et al. | |
| 2010/0050351 A1 | 3/2010 | Colantonio et al. | |
| 2010/0172794 A1 | 7/2010 | Ferlic et al. | |
| 2010/0204648 A1 | 8/2010 | Stout et al. | |
| 2010/0292673 A1 | 11/2010 | Korogi et al. | |
| 2011/0044850 A1 * | 2/2011 | Solomon | A61M 39/162 |
| | | | 422/28 |
| 2011/0150958 A1 | 6/2011 | Davis et al. | |
| 2011/0290799 A1 | 12/2011 | Anderson et al. | |
| 2012/0016318 A1 | 1/2012 | Hoang et al. | |

(56) References Cited

U.S. PATENT DOCUMENTS

| | | |
|---|---|---|
| 2012/0039764 A1 | 2/2012 | Solomon et al. |
| 2012/0039765 A1 | 2/2012 | Solomon et al. |
| 2012/0216360 A1 | 8/2012 | Rogers et al. |
| 2012/0283693 A1 | 11/2012 | Anderson et al. |
| 2015/0305974 A1* | 10/2015 | Ehrenreich .......... A61H 23/004 601/46 |

FOREIGN PATENT DOCUMENTS

| | | |
|---|---|---|
| JP | 2008253775 | 10/2008 |
| JP | 2009537250 | 10/2009 |
| JP | 2010516342 | 5/2010 |
| WO | 87/00441 A1 | 1/1987 |
| WO | 99/29173 A1 | 6/1999 |
| WO | 2006/019782 A2 | 2/2006 |
| WO | 2007/044760 A2 | 4/2007 |
| WO | 2007/137056 A2 | 11/2007 |
| WO | 2008/100950 A2 | 8/2008 |
| WO | 2008/157092 A1 | 12/2008 |
| WO | 2010/039171 A1 | 4/2010 |
| WO | 2010/143693 A1 | 12/2010 |
| WO | 2011/053924 A1 | 5/2011 |
| WO | 2011/066565 A1 | 6/2011 |
| WO | 2011/066586 A1 | 6/2011 |

OTHER PUBLICATIONS

"Patent Owner's Preliminary Response Under 37 C.F.R. .sctn. 42, 10," USPTO, Patent Trial and Appeal Board, *Excelsior Medical Corporation* v. *Becton, Dickinson and Company*, Case IPR2014-00880, U.S. Pat. No. 8,740,864, pp. 1-30, Sep. 16, 2014.

"Decision, Institution of Inter Partes Review, 37 C.F.R. .sctn. 42, 108," USPTO, Patent Trial and Appeal Board, *Excelsior Medical Corporation* v. *Becton, Dickinson and Company*, Case IPR2014-00880, U.S. Pat. No. 8,740,864, pp. 1-21, Nov. 25, 2014.

\* cited by examiner

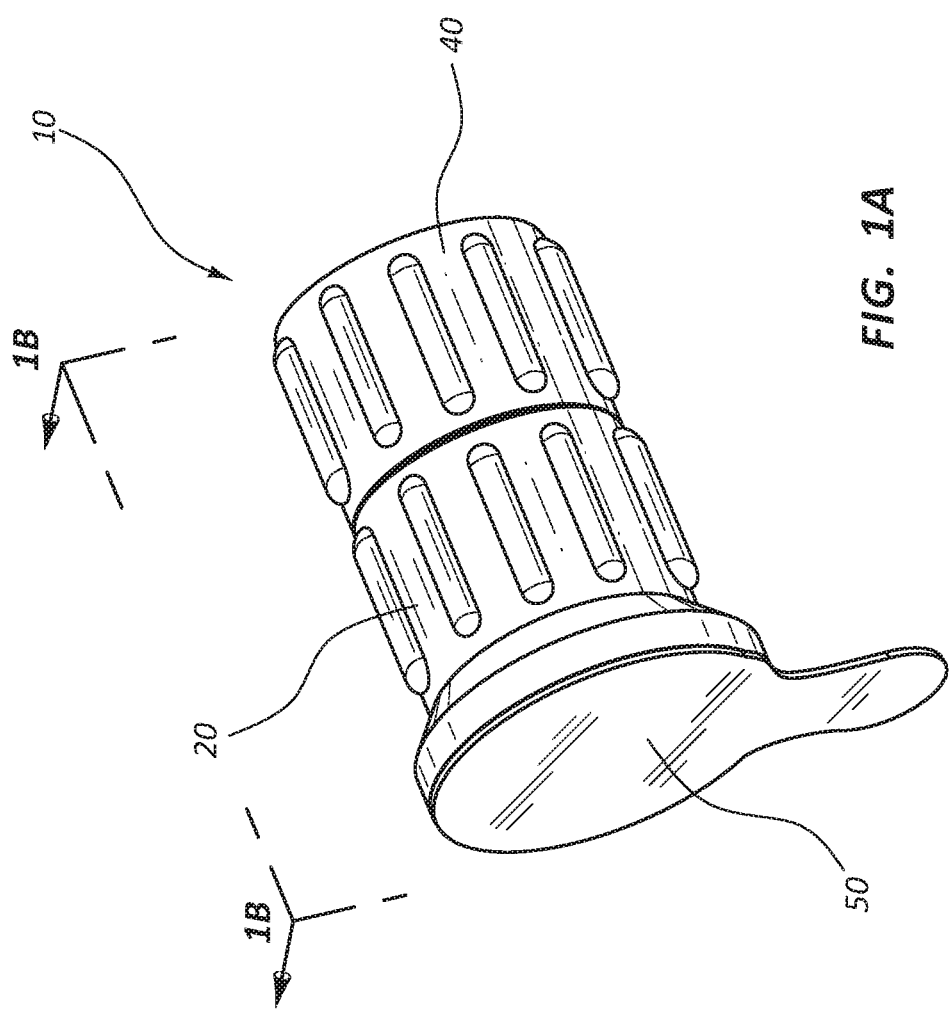

NEEDLELESS CONNECTOR AND ACCESS PORT DISINFECTION CLEANER AND ANTIMICROBIAL PROTECTION CAP

RELATED APPLICATIONS

This application is a continuation of U.S. patent application Ser. No. 13/766,540 filed Feb. 13, 2013, and titled NEEDLELESS CONNECTOR AND ACCESS PORT DISINFECTION CLEANER AND ANTIMICROBIAL PROTECTION CAP, and is incorporated herein by reference.

BACKGROUND OF THE INVENTION

Catheter-related bloodstream infections are caused by bacteria/fungi in patients with intravascular catheters. These infections are an important cause of illness and excess medical costs, as approximately 80,000 catheter-related bloodstream infections occur in U.S. intensive care units each year. In addition to the monetary costs, these infections are associated with anywhere from 2,400 to 20,000 deaths per year.

Guidelines from the Centers for Disease Control and Prevention describe various ways to limit catheter-related bloodstream infections in hospital, outpatient and home care settings. The guidelines address issues such as hand hygiene, catheter site care and admixture preparation. Despite these guidelines, catheter-related bloodstream infections continue to plague our healthcare system.

Protective caps incorporating various disinfectants and/or antimicrobial agents are one approach that has been implemented to prevent these infections at needleless connection points. While these caps are effective for long-term protection against pathogens, long-term exposure to the antimicrobial agent or disinfectant can cause damage to the needleless connection or access point of a medical device. In some instances, the antimicrobial agent is suspended in an alcohol solvent. The alcohol solvent used in the protective cap has been shown to cause device failure in many connector type devices. To prevent this damage, some protective caps are designed to permit the alcohol-base to evaporate from the protective cap. However, once the alcohol solvent has evaporated, the effectiveness of the protective cap is diminished.

Therefore, there is a need for an effective and inexpensive way to reduce the number of catheter-related infections for needleless connectors and access ports. Such methods and systems are disclosed herein.

BRIEF SUMMARY OF THE INVENTION

In some implementations, a protective cap is provided for antiseptically maintaining a patient fluid line access valve (i.e. access valve) or a needleless connector. In some instances, a protective cap is provided having a first cap that is removable coupled to a second cap, wherein the first cap has a first opening comprising a cavity in which is disposed a first pad. The first cap further comprises a coupling feature for receiving the second cap.

The second cap further includes a second opening having a cavity in which is disposed a second pad. The second opening further includes a compatible coupling feature whereby to receive or otherwise interconnect with the coupling feature of the first cap. The first and second caps each contain an antimicrobial composition that is configured to clean a needleless connector and/or an access port of an infusion system, such as an intravenous catheter assembly or intravenous tubing. In some implementations, the first opening of the first cap is temporarily sealed with a lid to prevent contamination and evaporation of the antimicrobial composition stored within the first pad. Further, in some instances the connection between the coupling features to the first and second caps prevents contamination of the second pad prior to use.

Some implementations of the present invention further include a protective cap system having a first and second cap that are independently coupled to different surfaces of an infusion device, such as a syringe. The first and second caps are independently removed from the syringe and applied to various surfaces to achieve short-term and long-term antimicrobial protection to various components of an infusion system.

Some implementations of the present invention further include a strip having a plurality of holes or openings for temporarily storing and organizing a plurality of protective caps. The protective caps comprise a first cap and a second cap, wherein each cap is configured to provide short-term and/or long-term antimicrobial protection to various components of an infusion system. In some instances, the openings of the first and second caps are sealed to a strip, rather than being inserted through an opening or hole.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1B:
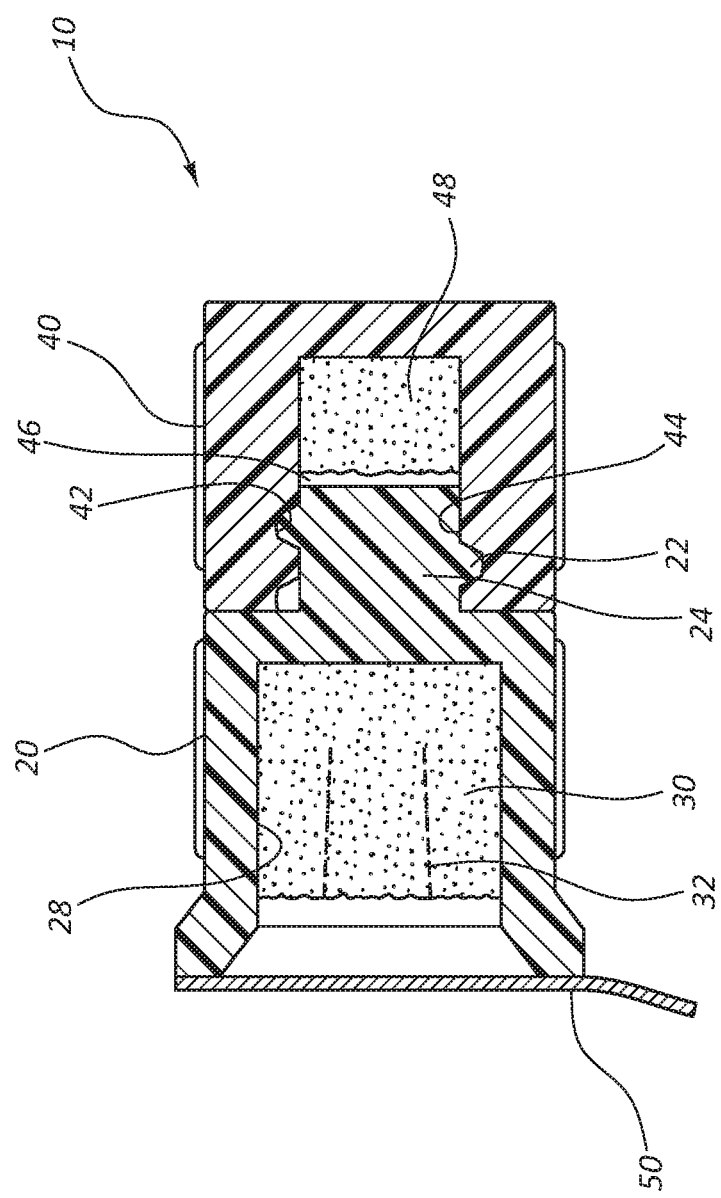
FIG. 1, shown in parts A and B, shows a protective cap device having a first cap threadedly coupled to a second cap in accordance with a representative embodiment of the present invention.

Referring now to FIGS. 1A and 1B, a protective cap 10 is shown. Generally, protective cap 10 comprises a first cap 20 that is coupled to a second cap 40. Each cap 20 and 40 is configured to receive or otherwise couple to a needleless connector or access port of a component of an infusion system. In some instances, first cap 20 is configured to receive a needleless connector without being attached to the needleless connector long-term. For example, first cap 20 may be used to quickly clean a needleless connector just prior to the needleless connector being coupled to a second medical device. In other instances, second cap 40 is configured to be attached to a needleless connector for long-term protection. For example, in some embodiments second cap 40 comprises a set of threads or other feature for securely receiving and retaining a portion of a needleless connector.

In some embodiments, first and second caps 20 and 40 are separated and applied to a needleless connector or access port to prevent pathogens from colonizing thereon. Further, in some embodiments first cap 20 is temporarily applied to a needleless connector or access port to kill any pathogens present thereon. The first cap 20 is then removed from the needleless connector or access port and the port is connected to, or accessed with a component of an infusion system. Upon removal of the component of the infusion system, first cap 20 is removed from second cap 40, and second cap 40 is fixedly coupled to the needleless connector or access port for long-term protection.

Protective cap 10 may comprise any material that is compatible for use in an infusion system. For example, in some embodiments protective cap comprises any of a number of types of plastic materials such as polycarbonate, polypropylene, polyethylene, glycol-modified polyethylene terephthalate, acrylonitrile butadiene styrene or any other moldable plastic material used in medical devices.

In some embodiments, first cap 20 and second cap 40 are selectively coupled to form protective cap 10. For example, in some embodiments first cap 20 comprises a set of threads 22 that is configured to interlock with a set of mating threads 42 on second cap 40. In some instances, first cap 20 comprises a post 24 that supports threads 22 in a configuration that permits an opening 46 of second cap 40 to receive post 24 and threads 22. In some instances, mating threads 42 comprises a set of female threads that are formed into an inner surface 44 of second opening 46. Other embodiments include a cavity (not shown) on first cap 20 having internal threads and a width sufficient to receive external threads (not shown) located on an outer surface of second cap 40.

First cap 20 further comprises a first opening 28 having a first pad 30 disposed therein. First pad 30 generally comprises an absorbent material, such as a sponge or other non-woven material. In some instances, first pad 30 comprises an absorbent, woven material. First pad 30 may be secured into first opening by mechanical interference. Alternatively, first pad 30 may be secured into first opening 28 via a biocompatible adhesive.

In some instances, first pad 30 further comprises a central, cylindrical cutout 32 that is not directly, physically coupled to the inner surface of opening 28. Rather, cutout 32 may be collapsed or compressed to provide a central hole or cavity within first pad 30. For example, cutout 32 may be compressed by inserting a device into opening 28, such as a needleless connector or access port. In this way, a tip and sides of the inserted device may be simultaneously contacted by first pad 30 without disrupting the bond between first pad 30 and the inner surface of second opening 28.

Second cap 40 further comprises a second pad 48 that is fixedly seated into second opening 46. Second pad 48 generally comprises a woven or non-woven absorbent material, such as a sponge. In some embodiments, second pad 48 is positioned within second opening 46 so that second pad 48 does not contact post 24 when first cap 20 is threadedly coupled to second cap 40. In other embodiments, second pad 48 is compressed within second opening 46 by post 24 when first cap 20 is threadedly coupled to second cap 40. Upon separation of first and second caps 20 and 40, second pad 48 is uncompressed and expands such that second pad 48 contacts and/or overlaps threads 42. This feature may be desirable for treating threads 42 with an antimicrobial composition stored in second pad 48.

First and second pads 30 and 48 may comprise an antimicrobial composition that is effective in preventing growth and colonization of pathogens, and that is safe for use in an infusion system. An antimicrobial composition in accordance with the present invention generally comprises an antimicrobial or biocidal agent effective against various forms and strains of bacteria which may cause infection within a patient. The terms "biocidal agent" "antimicrobial agent" or "biocide," as used herein refer to an agent that destroys, inhibits and/or prevents the propagation, growth, colonization and multiplication of unwanted organisms. The term "organism" includes, but is not limited to, microorganisms, bacteria, undulating bacteria, spirochetes, spores, spore-forming organisms, gram-negative organisms, gram-positive organisms, yeasts, fungi, molds, viruses, aerobic organisms, anaerobic organisms and mycobacteria.

Specific examples of such organisms include the fungi *Aspergillus niger, Aspergillus flavus, Rhizopus nigricans, Cladosprorium herbarium, Epidermophyton floccosum, Trichophyton mentagrophytes, Histoplasma capsulatum*, and the like; bacteria such as *Pseudomanas aeruginosa, Escherichia coli, Proteus vulgaris, Staphylococcus aureus, Staphylococcus epidermis, Streptococcus faecalis, Klebsiella, Enterobacter aerogenes, Proteus mirabilis*, other gram-negative bacteria and other gram-positive bacteria, mycobactin and the like; and yeast such as *Saccharomcyces cerevisiae, Candida albicans*, and the like. Additionally, spores of microorganisms, viruses and the like are organisms within the scope of the present invention.

Antimicrobial or biocide agents suitable for use in the present invention include, but are not limited to phenol, quaternary ammonium, guanidine, taurolidine, parachlorometaxylenol, silver sulfadiazine, silver oxide, silver nitrate, pyridinium, benzalkonium chloride, cetrimide, benethonium chloride, cetylpyridinium chloride, dequalinium acetate, dequalinium chloride, and chloroxylenol. Further, in some embodiments a biocide agent comprises a microbial agent selected from chlorhexidine base, chlorhexidine gluconate, chlorhexidine acetate, chlorhexidine hydrochloride, chlorhexidine dihydrochloride, dibromopropamidine, halogenated diphenylalkanes, carbanilide, salicylanilide, tetrachlorosalicylanilide, trichlorocarbanilide, and mixtures thereof. Still further, in some embodiments a biocide agent comprises a microbial agent selected from chlorhexidine dihydrochloride, chlorhexidine gluconate, chlorhexidine acetate, chlorhexidine diacetate, triclosan, chloroxylenol, dequalinium chloride, benzethonium chloride, benzalkonium chloride, and combinations thereof.

In some embodiments first or second pads 30 and 48 comprise a liquid antimicrobial composition. In other embodiments, first or second pads 30 and 48 comprise a dehydrated antimicrobial composition, wherein the dehydrated antimicrobial composition is activated upon rehydration with a fluid, such as water, alcohol, blood, or another liquid common to infusion therapies. In some instances, lid 50 provides a fluid tight seal for first opening 28, thereby preventing premature evaporation of an antimicrobial composition stored in first pad 30. Further still, in some instances interlocked threads 42 and 22 provide a fluid tight seal for second opening 46, thereby preventing premature evaporation of an antimicrobial composition stored in second pad 48.

In some embodiments, first pad 30 comprises a liquid antimicrobial composition, wherein lid 50 prevents premature evaporation of the antimicrobial agent prior to use. In other embodiments, second pad 48 comprises a dehydrated antimicrobial composition, wherein the dehydrated antimicrobial composition is activated upon rehydration with a fluid, such as water, alcohol, blood, or another liquid common to infusion therapies. In some instances, the dehydrated state of second pad 48 prevents long-term exposure of the needleless connector to a liquid, alcohol-based antimicrobial composition. Contact between a dehydrated composition within second pad 48 and the surface of the needleless connector provides antimicrobial protection without causing damage thereto. As such, damage to the needleless connector caused by a liquid, alcohol-based antimicrobial composition is prevented. Further, the dehydrated state of the second pad 48 wicks or removes fluids from the needleless connector, thereby preventing damage and/or colonization of microbes on the needleless connector. Once wicked into second pad 48, the dehydrated antimicrobial agent is activated and microbes within the fluid are neutralized.

In some instances, first and second pads 30 and 48 each comprise an identical antimicrobial composition. In other instances, first pad 30 comprises a first antimicrobial composition, and second pad 48 comprises a second antimicrobial composition, wherein the first and second antimicrobial compositions are different. Thus, first cap 20 may be used to provide a first type of disinfection, and second cap 40 may be used to provide a second type of disinfection.

Prior to use, first and second caps 20 and 40 are threadedly coupled together and first opening 28 is sealed with a lid 50, such as a piece of foil, a thin polymer membrane, a foil-backed piece of paper, or a polymer-backed piece of paper. To use protective cap 10, a user may remove lid 50 to expose first pad 30 seated in first opening 28. A user may insert an access valve or a needleless connector into first opening 28 and into contact with first pad 30. The access valve or needleless connector is treated with the antimicrobial composition as the surfaces are contacted with first pad 30.

Figure 2A:
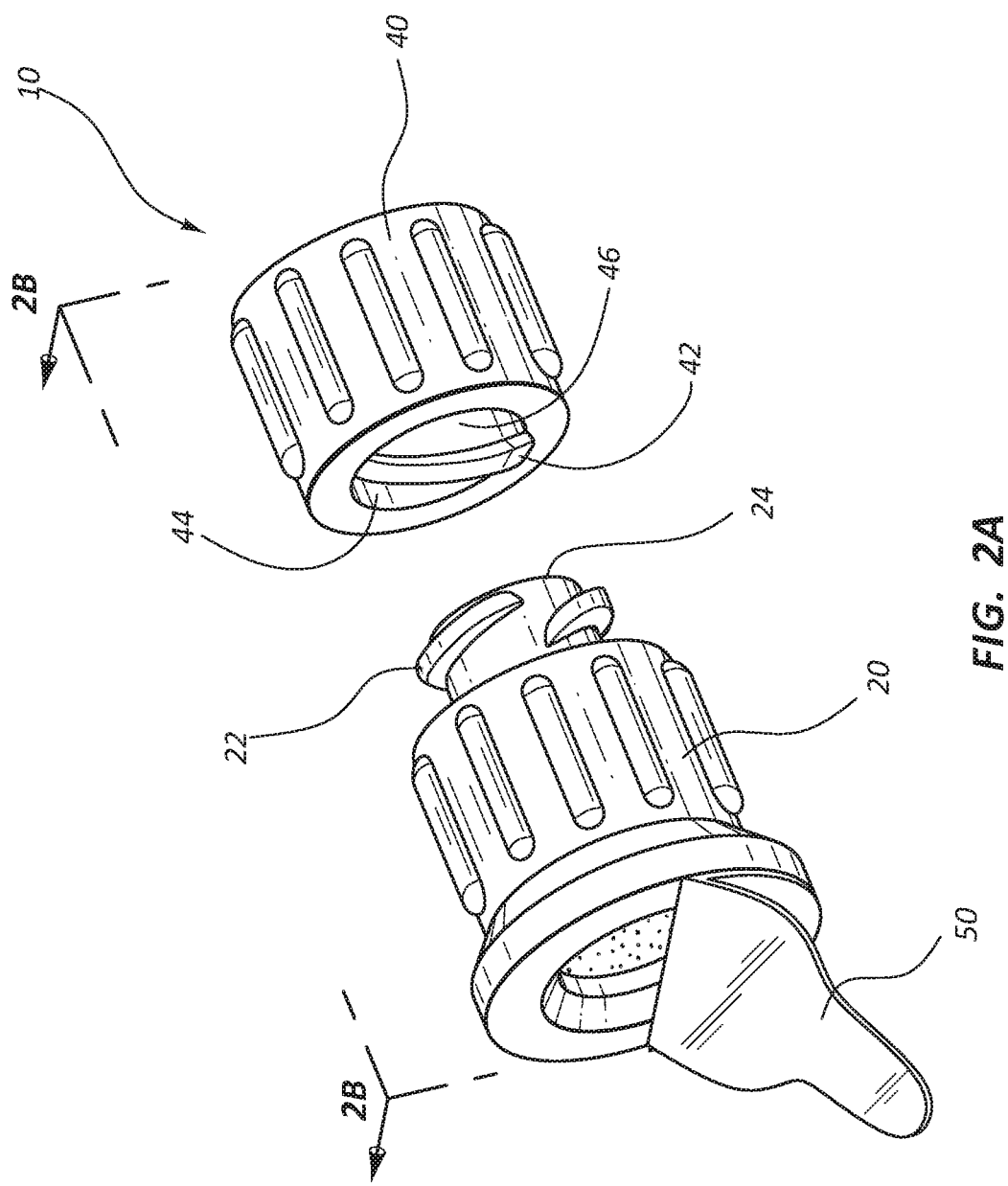
FIG. 2, shown in parts A and B, shows a protective cap device having a first cap unthreaded from a second cap in accordance in accordance with a representative embodiment of the present invention.
Figure 2B:
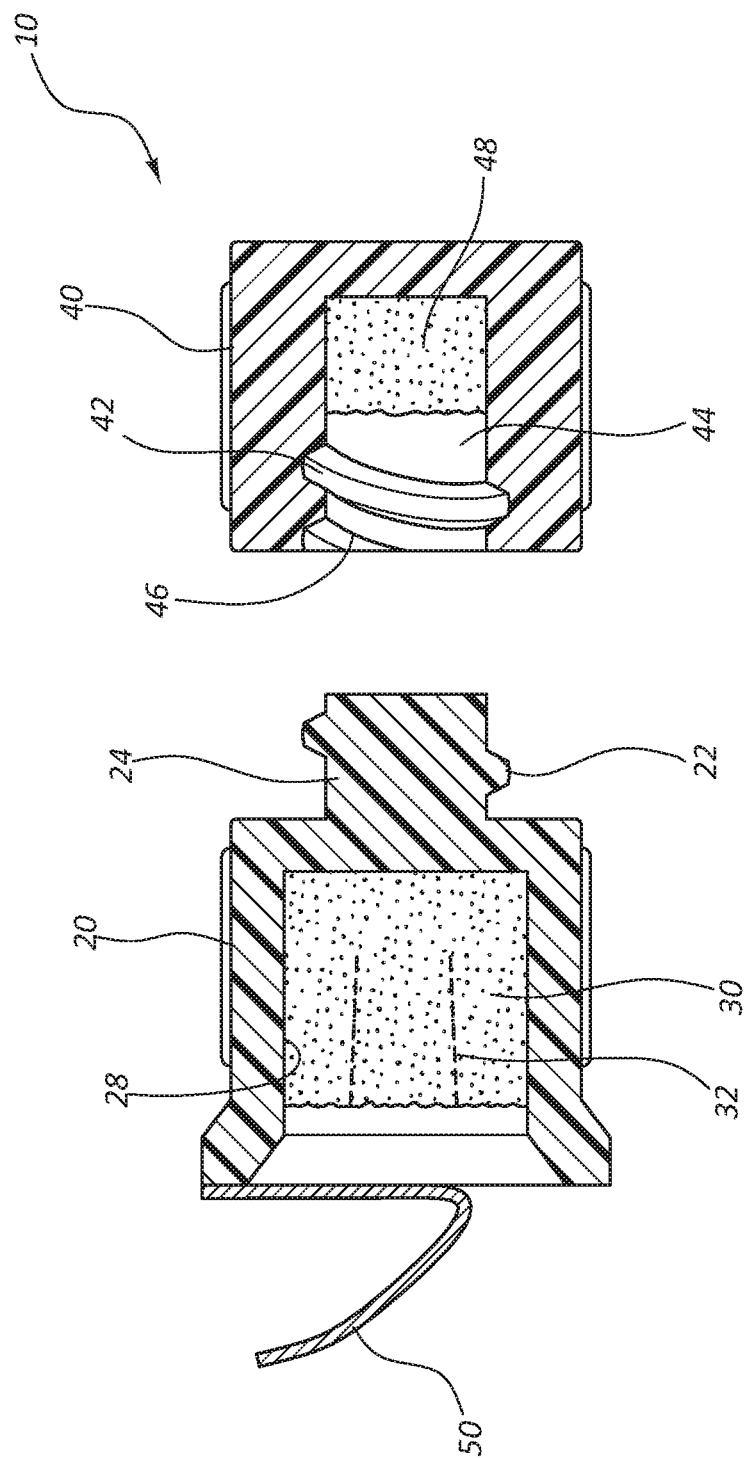

Once the access valve or needleless connector is cleaned, it may be connected to another component of an infusion system. Upon disconnecting the access valve or needleless connector, second cap 40 is removed or unthreaded from first cap 20, as shown in FIGS. 2A and 2B. Second cap 40 is attached to the disconnected valve or connector to provide antimicrobial protection thereto during long-term storage.

For example, in some embodiments the access valve or needleless connector comprises a set of threads that are compatibly received by the set of mating threads 42 located on inner surface 44 of second cap 40. When second cap 40 is threadedly connected to the valve or connector, second pad 48 contacts the valve or connector to provide antimicrobial cleaning and protection. The threaded connection between second cap 40 and the access valve or connector further prevents exposure of the needleless connector to microbes or other contaminants. In some instances, the threaded connection prevents exposure to fluids which may leak from the valve or connector.

Figure 3:
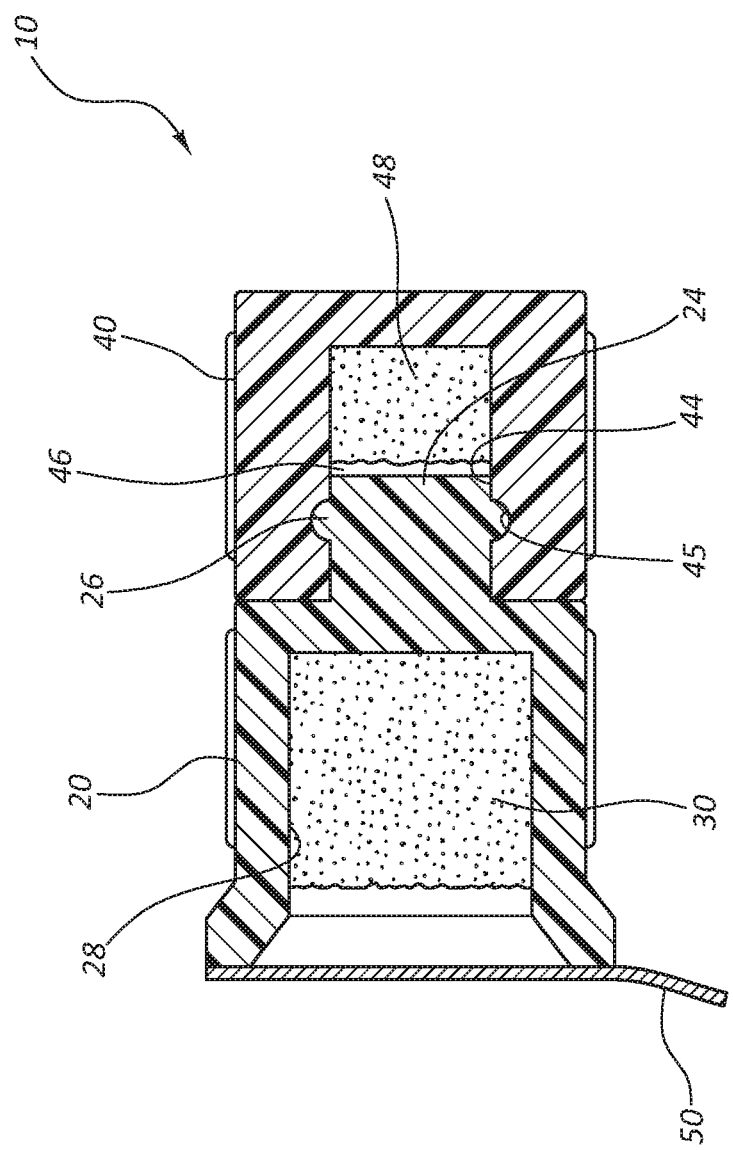
FIG. 3 shows a cross-section view of a protective cap device having a first cap mechanically coupled to a second cap in accordance with a representative embodiment of the present invention.

Referring now to FIG. 3, first and second caps 20 and 40 may be selectively coupled by any means. For example, in some embodiments post 24 of first cap 20 comprises an annular ring 26 that snaps into an annular groove 45 that is formed on inner surface 44 of second cap 40. The interaction between ring 26 and groove 45 provide a mechanical connection that may be separated by pulling apart the first and second caps 20 and 40. Ring 26 and groove 45 further provide a fluid tight seal, thereby preventing evaporation of an antimicrobial composition stored in second pad 48.

In some instances, an access valve or needleless connection further comprises an annular ring that is compatibly received by annular groove 45 when second cap 40 is placed thereon. In other embodiments, second cap 40 is retained by the access valve or needleless connection via mechanical interference or friction fit.

Figure 4A:
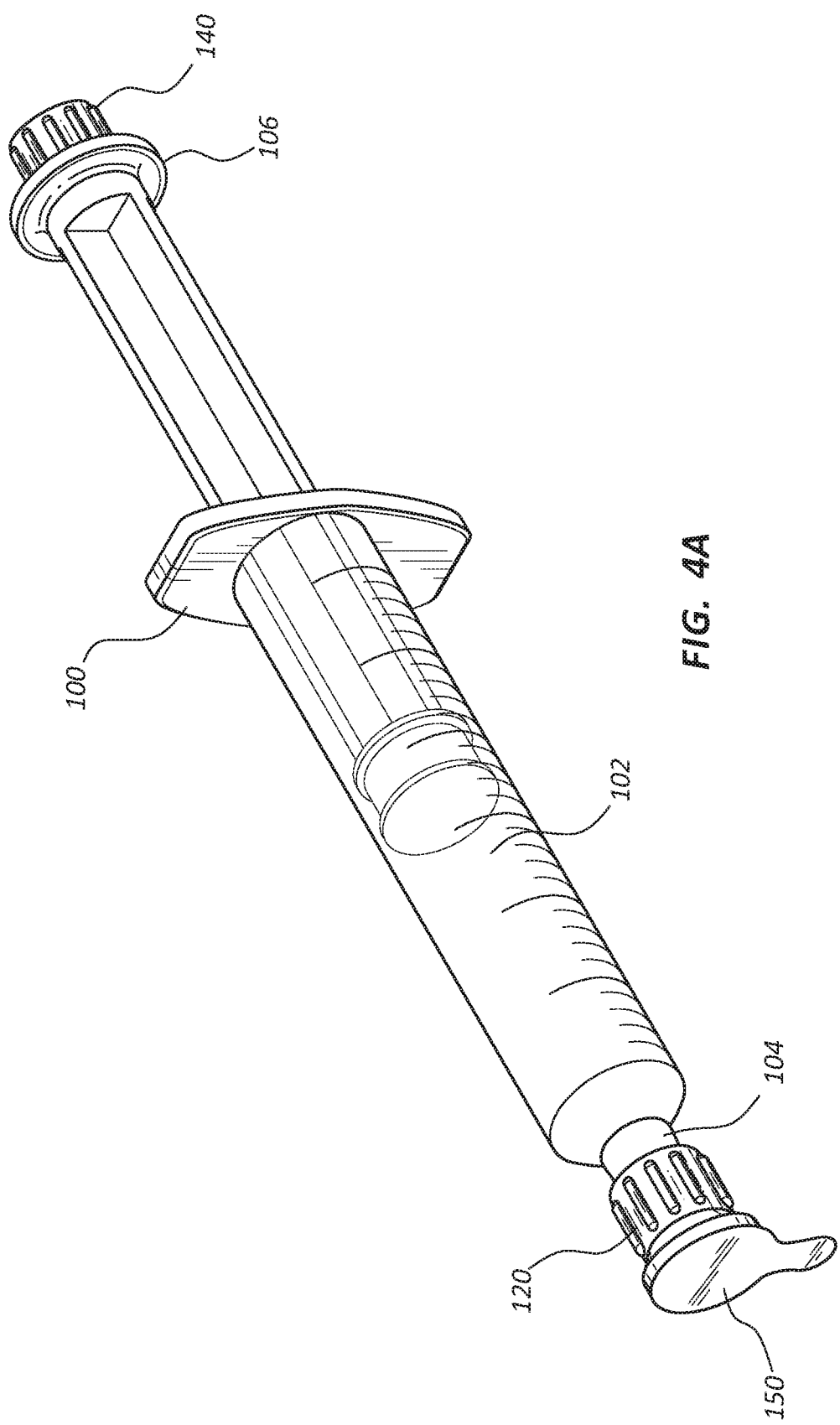
FIG. 4, shown in parts A and B, shows a needleless device fitted with a protective cap device having a first cap coupled to a nozzle of the needleless device, and a second cap stored on plunger of the needleless device in accordance with a representative embodiment of the present invention.
Figure 4B:
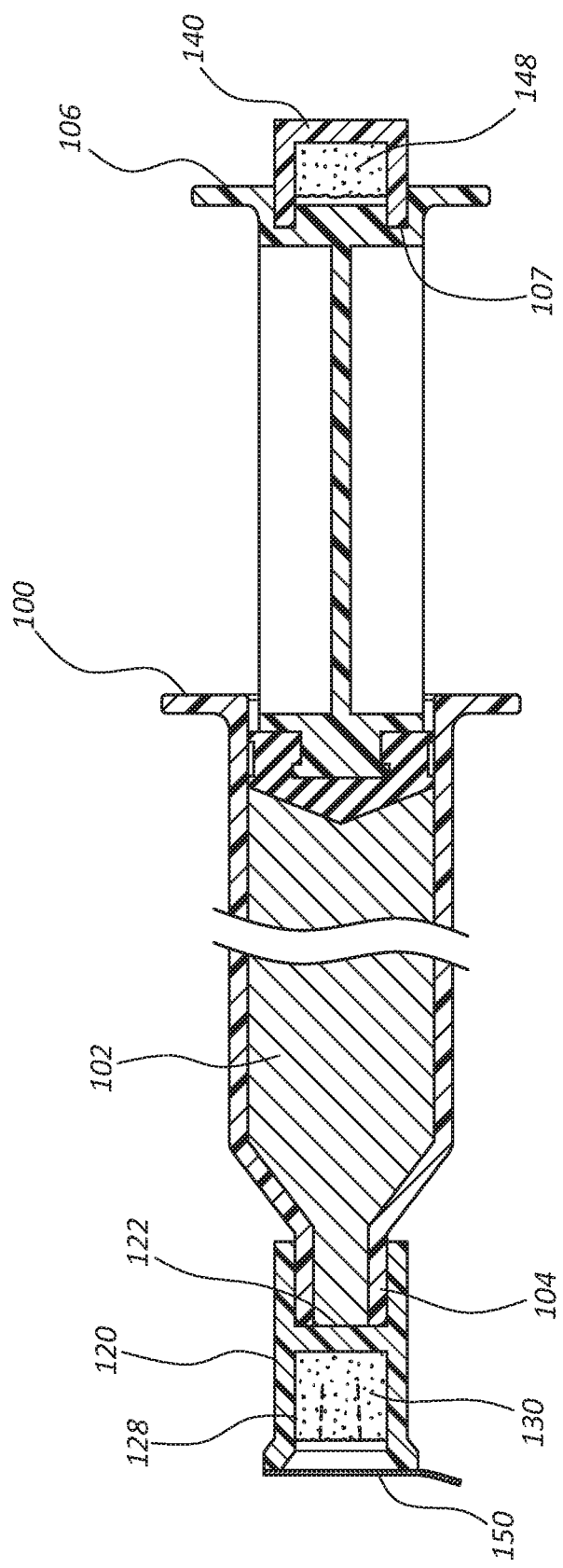

In some embodiments, a protective cap comprising a set of individual caps may be configured for attachment to a pre-filled syringe 100, as shown in FIGS. 4A and 4B. In some instances it is desirable to provide a syringe 100 that is pre-filled with a desired liquid 102. In these instances, it is further desirable that the liquid 102 and the needleless connector or nozzle 104 remain free from pathogens before and during use.

Accordingly, in some embodiments a first cap 120 is provided having a receptacle 122 for receiving nozzle 104 of syringe 100. Prior to capping nozzle 104 with receptacle 122 of first cap 120, receptacle 122 is sterilized. This prevents contamination of nozzle 104 and fluid 102, as may be desired. Sterilization of receptacle 122 may be achieved by any known method in the art.

First cap 120 further comprises a first opening 128 in which is seated a first pad 130. First pad 130 may comprises an antimicrobial composition that is configured to clean an access port (not shown) intended to receive nozzle 104 of syringe 100. First cap 120 may further include a lid 150 to protect first pad 130 and prevent evaporation of the antimicrobial composition prior to use.

The protective cap may further include a second cap 140 that is removable coupled to a portion of syringe 100. For example, in some embodiments cap 140 is coupled to the plunger 106 of syringe 100. Plunger 106 may comprise a circular groove 107 that is configured to receive and temporarily store second cap 140. In some embodiments, second cap 140 is threadedly secured to plunger 106. In other embodiments, second cap 140 is coupled to plunger 106 via a friction fit.

The connection between second cap 140 and syringe 100 prevents evaporation and/or contamination of an antimicrobial agent stored in second cap 140. For example, in some instances second cap 140 comprises a second pad 148 containing an antimicrobial composition. The connection between second cap 140 and syringe 100 provides a fluid tight seal for second pad 148. The connection between second cap 140 and syringe 100 further provides convenient placement of second cap 140 for access by a user of the syringe.

For example, in some embodiments a user of syringe 100 first removes lid 150 from first cap 120 to expose first pad 130. First pad 130 is then used to clean an access port of an infusion system. The access port is clean by inserting the access portion within second opening 128 to contact first pad 130. First cap 120 is then removed from nozzle 104. Nozzle 104 is then connected to the access port.

In some instances, a desired volume of fluid 102 is injected into the infusion system via an access port. Where the desired volume comprises the entire contents of syringe 100, second cap 140 may be removed from plunger 106 following injection of liquid 102, and connected to the access port to prevent subsequent contamination thereof. Where the desired volume comprises only a portion of the contents of syringe 100, and where it is desirable to use the remaining contents of syringe 100 at a later time, second cap 140 may be removed from plunger 106 and coupled to nozzle 104 to prevent subsequent contamination thereof. Second cap 140 further prevents contamination of the remaining fluid 102. At the time in which it is desirable to inject the remaining fluid 102 into the access port, second cap 140 is removed from nozzle 104 and is used to clean the access port. The clean nozzle 104 is then inserted into the clean access port, and the remaining fluid is injected without introducing microbes into the infusion system. In some embodiments, second cap 140 is then coupled to the access port to provide long-term antimicrobial protection.

Figure 5B:
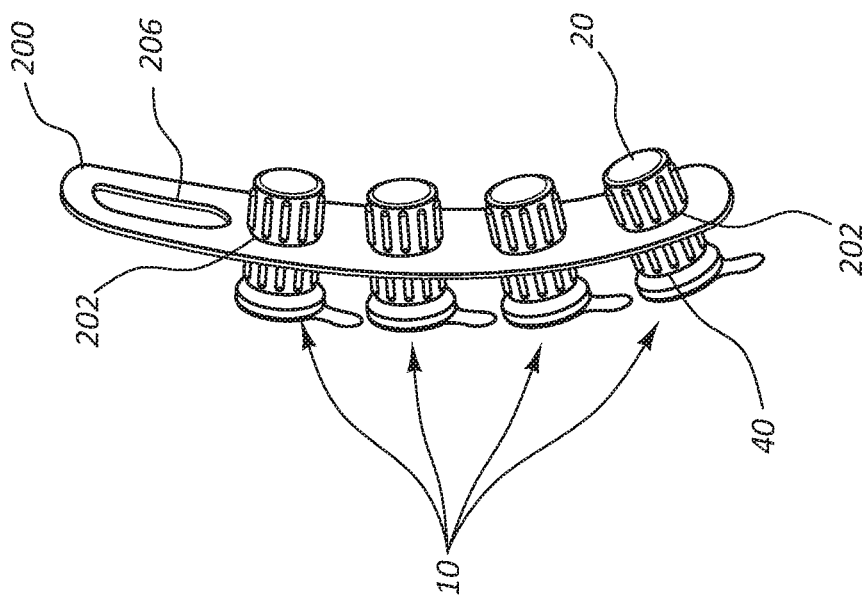
FIG. 5, shown in parts A and B, shows perspective and detailed views of a plurality of protective caps arranged on a strip for conveniently providing multiple caps for use in protecting a needleless connector in accordance with a representative embodiment of the present invention.
Figure 5A:
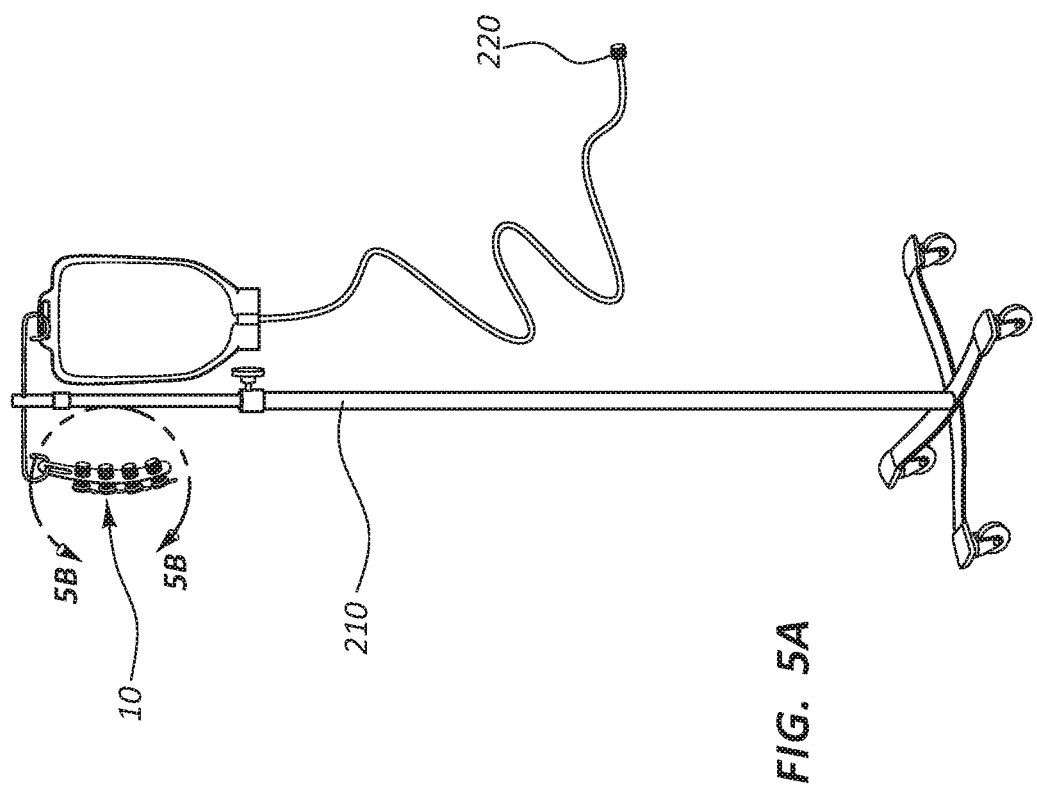

Referring now to FIGS. 5A and 5B, a plurality of protective caps 10 is provided on a strip 200 that is configured to be removable coupled to a medical device, such as an IV stand 210. This configuration may be desirable for situations where a needless connector 220 may require repeated cleanings over a period of use. In some embodiments, strip 200 comprises a plurality of holes or openings 202 through which each cap is fitted. In some instances, each cap comprises a first cap 20 and a second cap 40, wherein strip 200 is inserted between the two caps.

In some instances, cap 10 is removed from strip 200 by separating first cap 20 from second cap 40. In other instances, cap 10 is removed from strip 200 by stretching or biasing opening 202 via pushing or pulling cap 10. First and second caps 20 and 40 may be used to clean needleless connector 220, in accordance with the teachings above. Upon subsequent cleanings, the first and second caps of a first protective cap are discarded and an additional protective cap is removed from strip 200 and used. An enlarged opening 206 may be provided to assist in coupling strip 200 to a desired medical device 210. In some embodiments, strip 200 is temporarily secured to a medical device via an adhesive strip or other suitable means.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A device for antiseptically maintaining a patient fluid line access valve, the device comprising:
    a first cap comprising a distal end and a proximal end, wherein the distal end of the first cap comprises a first opening having a first pad disposed therein, and the proximal end comprises a post having a solid cross-section and extending outwardly from the proximal end, the solid cross-section comprising a coupling feature; and
    a second cap comprising a distal end and a proximal end, wherein the distal end of the second cap comprises a second receptacle having a second pad disposed therein, wherein the second receptacle comprises a compatible coupling feature in fluid communication with the second pad and configured to receive the coupling feature on the solid cross-section of the post of the first cap to form a fluid tight seal.

2. The device of claim 1, wherein the first cap comprises a removable lid that covers the first opening.

3. The device of claim 2, wherein the removable lid comprises at least one of a foil lidding material and a polymer lidding material.

4. The device of claim 1, wherein the first opening is configured to receive an access portion of a patient fluid line access valve.

5. The device of claim 4, wherein the first opening includes a set of threads that is configured to receive a compatible set of threads on the access portion of the patient fluid line access valve.

6. The device of claim 1, further comprising a syringe having a first end comprising a spout and a second end comprising a base of a plunger, wherein the base of the plunger includes a circular groove that receives the distal end of the second cap to thereby couple the second cap to the plunger.

7. The device of claim 1, further comprising a first antimicrobial solution applied to the first pad and a second antimicrobial solution applied to the second pad.

8. The device of claim 7, wherein the first antimicrobial solution comprises a wet solution selected from at least one of a first antimicrobial agent from approximately 0.01% to approximately 10.0% (v/v), and an alcohol from approximately 50% to approximately 99.99% (v/v), wherein the second antimicrobial solution comprises a dry antimicrobial coating comprising a second antimicrobial agent.

9. The device of claim 8, wherein the first and second antimicrobial agents are selected from the group consisting of chlorhexidine acetate, chlorhexidine gluconate, PVP-I, Triclosan, PCMX, BEC, BAC, antibiotic, Octinidine, and suitable salts thereof.

10. The device of claim 7, wherein the first antimicrobial solution comprises a wet, water-based solution, comprising:
    a first antimicrobial agent from approximately 0.01% to approximately 10.0% (v/v);
    an alcohol solvent from approximately 1% to approximately 10% (v/v); and
    water from approximately 90% to approximately 99% (v/v); and
    wherein the second antimicrobial solution comprises a dry antimicrobial coating comprising a second antimicrobial agent.

11. The device of claim 10, wherein the first and second antimicrobial agents are selected from the group consisting of chlorhexidine acetate, chlorhexidine gluconate, PVP-I, Triclosan, PCMX, BEC, BAC, antibiotic, Octinidine, and suitable salts thereof.

12. The device of claim 1, wherein the first pad comprises a central, cylindrical cutout configured to compress to provide a central cavity in response to a device being inserted into the first opening, wherein the central cylindrical cutout does not provide the central cavity when the first pad is uncompressed.

* * * * *